US009133100B2

(12) United States Patent
Sakaki et al.

(10) Patent No.: US 9,133,100 B2
(45) Date of Patent: Sep. 15, 2015

(54) METHOD FOR SYNTHESIZING RARE EARTH METAL EXTRACTANT

(75) Inventors: Kazuaki Sakaki, Echizen (JP); Hiroto Sugahara, Echizen (JP); Tetsuya Kume, Echizen (JP); Masaki Ohashi, Joetsu (JP); Hirochika Naganawa, Naka-gun (JP); Kojiro Shimojo, Naka-gun (JP)

(73) Assignees: SHIN-ETSU CHEMICAL CO., LTD., Tokyo (JP); JAPAN ATOMIC ENERGY AGENCY, Ibaraki (JP)

( * ) Notice: Subject to any disclaimer, the term of this patent is extended or adjusted under 35 U.S.C. 154(b) by 0 days.

(21) Appl. No.: 13/808,220

(22) PCT Filed: Jul. 1, 2011

(86) PCT No.: PCT/JP2011/065172
§ 371 (c)(1),
(2), (4) Date: Jan. 3, 2013

(87) PCT Pub. No.: WO2012/005182
PCT Pub. Date: Jan. 12, 2012

(65) Prior Publication Data
US 2013/0123534 A1    May 16, 2013

(30) Foreign Application Priority Data

Jul. 5, 2010  (JP) .................. 2010-153180

(51) Int. Cl.
| C07C 229/00 | (2006.01) |
| C07C 231/02 | (2006.01) |
| C07C 235/06 | (2006.01) |
| C22B 47/00 | (2006.01) |
| C22B 59/00 | (2006.01) |
| C22B 3/08 | (2006.01) |
| C22B 3/44 | (2006.01) |

(52) U.S. Cl.
CPC ............. C07C 231/02 (2013.01); C07C 235/06 (2013.01); C22B 47/00 (2013.01); C22B 59/00 (2013.01); C22B 3/08 (2013.01); C22B 3/44 (2013.01); *Y02W 30/54* (2013.01)

(58) Field of Classification Search
CPC ...... C07C 231/02; C07C 235/06; C22B 3/08; C22B 3/44; C22B 47/00; C22B 59/00
USPC ....................................................... 562/567
See application file for complete search history.

(56) References Cited

U.S. PATENT DOCUMENTS 4,123,538 A    10/1978    Umen

FOREIGN PATENT DOCUMENTS

| CN | 1613846 A | | 5/2005 |
| CN | 1613846 A | * | 5/2005 |
| JP | 54-046719 A | | 4/1979 |
| JP | 2007 327085 | * | 12/2007 |
| JP | 2007-327085 A | | 12/2007 |

OTHER PUBLICATIONS

Organic Chemistry (Organic Chemistry I, Chem 141, 2009, downloaded from the internet on Oct. 29, 2013).*
Qiang Wang et al. (Synthesis of methylenebisamides using CC- or DCMT-activated DMSO, Beilstein Journal of Organic Chemistry 2008, 4, No. 51.)*
Toluene Xylene 2003 (downloaded from Internet Sep. 23, 2014.*
CN 1613846A 2005 translation conducted on the STIC website on Oct. 28, 2013.*
JP 2007 327085 translation conducted on the Japan Patent website on Oct. 28, 2013.*
Schlesinger et al. (SCMTR: A Chloride-Selective, Membrane-Anchored Peptide Channel that Exhibits Voltage Gating, Journal of the American Chemical Society, vol. 124, 2002).*
Pajewski, Robert et al., "Pore formation in and enlargement of phospholipid liposomes by synthetic models of ceramides and sphingomyelin", Bioorganic & Medicinal Chemistry, vol. 13, 2005, p. 29-37.
International Search Report of PCT/JP2011/065172, mailing date of Aug. 16, 2011.

* cited by examiner

*Primary Examiner* — Yevegeny Valenrod
*Assistant Examiner* — Blaine G Doletski
(74) *Attorney, Agent, or Firm* — Westerman, Hattori, Daniels & Adrian, LLP

(57) ABSTRACT

A rare earth metal extractant containing, as the extractant component, dialkyldiglycol amide acid which is excellent in breaking down light rare earth elements is reacted in diglycolic acid (X mol) and an esterification agent (Y mol) at a reaction temperature of 70° C. or more and for a reaction time of one hour or more such that the mol ratio of Y/X is 2.5 or more, and is subjected to vacuum concentration. Subsequently, a reaction intermediate product is obtained by removing unreacted products and reaction residue. Then a nonpolar or low-polar solvent which is an organic solvent for forming an organic phase during solvent extraction of the rare earth metal and which is capable of dissolving dialkyldiglycol amide acid is added as the reaction solvent, and the reaction intermediate product is reacted with dialkyl amine (Z mol) such that the mol ratio of Z/X is 0.9 or more.

30 Claims, 2 Drawing Sheets

METHOD FOR SYNTHESIZING RARE EARTH METAL EXTRACTANT

TECHNICAL FIELD

This invention relates to a method for synthesizing a rare earth metal extractant, especially suited for the extraction and separation of at least two of light rare earth elements (La, Ce, Pr, Nd, Sm, and Eu), or at least one of the light rare earth elements and at least one of other rare earth elements (inclusive of Y).

BACKGROUND ART

In the modern society, rare earth elements are used in a wide variety of applications, for example, as rare earth magnets, phosphors, and electronic materials in nickel hydrogen batteries. With respect to the current supply of rare earth elements, a crisis of the rare earth resource is highlighted because the producers are limited, the price lacks stability, and the demand is expected to surpass the supply in the near future. For these reasons, many attempts are made to reduce the amount of rare earth element used and to develop a replacement. At the same time, it is desired to establish a recycle system for recovering rare earth elements as one valuable from in-process scraps produced during manufacture of products and municipal wastes like electric and electronic appliances collected from cities. Also there is an urgent need for the research and development of new rare earth mines.

Known methods for separating rare earth elements include column extraction (or solid-liquid extraction) using ion exchange resins, and solvent extraction (or liquid-liquid extraction) using metal extractants. Although the column extraction (or solid-liquid extraction) method is simple in apparatus and easy in operation as compared with the solvent extraction method, it is small in extraction capacity and discourages rapid treatment. The column extraction method is thus used in the removal of a metal when the concentration of a metal to be extracted in a solution is low, that is, when the metal to be extracted is present as an impurity, as well as in the waste water treatment. On the other hand, the solvent extraction (or liquid-liquid extraction) method needs a complex apparatus and cumbersome operation as compared with the column extraction method, but provides for a large extraction capacity and rapid treatment. Thus the solvent extraction method is often used in industrial separation and purification of metal elements. For the separation and purification of rare earth elements that requires efficient treatment of a large volume through continuous steps, the solvent extraction method capable of such efficient treatment is often used.

In the solvent extraction method, a water phase consisting of an aqueous solution containing metal elements to be separated is contacted with an organic phase consisting of an extractant for extracting a selected metal element and an organic solvent for diluting the extractant. Then the metal element is extracted with the extractant for separation.

Known metal extractants used in the art include tributyl phosphate (TBP), carboxylic acids (e.g., Versatic Acid 10), phosphoric acid esters, phosphonic acid compounds, and phosphinic acid compounds. A typical phosphoric acid ester is di-2-ethylhexylphosphoric acid (D2EHPA), a typical phosphonic acid compound is 2-ethylhexylphosphoric acid-mono-2-ethylhexyl ester (PC-88A by Daihachi Chemical Industry Co., Ltd.), and a typical phosphinic acid compound is bis(2,4,4-trimethylpentyl)phosphoric acid (Cyanex 272 by Cytec Industries). These extractants are commercially available and commonly used.

The separation efficiency of the solvent extraction method depends on a separation ability of the metal extractant, specifically a separation factor thereof. As the separation factor is higher, the separation efficiency of the solvent extraction method is higher, which enables simplification of separating steps and scale-down of the separation apparatus, making the process efficient and eventually leading to a cost reduction. A low separation factor, on the other hand, makes the separation process complex and poses a need for a large-scale separation apparatus.

Even PC-88A which is known to have a high separation factor for rare earth elements among the currently commercially available metal extractants has a low separation factor between elements of close atomic numbers, for example, a separation factor of less than 2, specifically about 1.4 between neodymium and praseodymium which are allegedly most difficult to separate among rare earth elements. The separation factor of this value is not sufficient for separation between neodymium and praseodymium. To separate them at an acceptable purity, a large-scale apparatus must be installed at the expense of cost. For more efficient separation of these elements, there is a desire for the development of a metal extractant having a higher separation factor than in the prior art and an extracting/separating method using the same.

Dialkyl diglycol amic acids are known from Patent Document 1: JP-A 2007-327085 as the metal extractant having a high separation factor with respect to rare earth elements, specifically light rare earth elements such as lanthanum (La), cerium (Ce), praseodymium (Pr), neodymium (Nd), and samarium (Sm). Using this extractant in solvent extraction, the extraction/separation step of rare earth elements, specifically light rare earth elements can be made more efficient. In fact, better results are obtained from the extraction/separation step of light rare earth elements using dialkyl diglycol amic acid on a laboratory scale.

When dialkyl diglycol amic acid was used as the metal extractant, satisfactory results were confirmed in a light rare earth element extraction/separation experiment which was conducted at a rare earth element concentration ($C_A$: 0.01 mol/L≤$C_A$≤0.7 mol/L) and a corresponding metal extractant concentration ($C_A$: 0.1 mol/L≤$C_0$≤1.5 mol/L) which were practical operating conditions of the rare earth element separating process and in a light rare earth element extraction/separation experiment using a countercurrent multi-stage mixer/settler of a practically operating apparatus.

The dialkyl diglycol amic acid exhibits a satisfactory separation factor in its performance as the metal extractant for separating light rare earth elements, as mentioned above, and its operating conditions have been surveyed. However, its synthesis has not been fully established.

The known method for synthesizing the dialkyl diglycol amic acid follows the reaction scheme below.

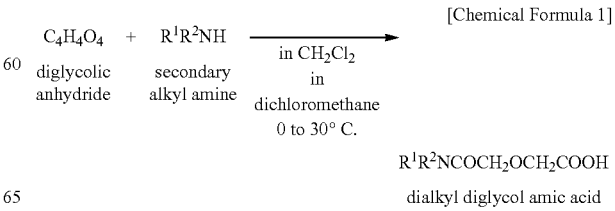

[Chemical Formula 1]

Herein $R^1$ and $R^2$ are each independently alkyl, and at least one is a straight or branched alkyl group of at least 6 carbon atoms.

First, diglycolic anhydride is suspended in dichloromethane. A secondary alkylamine in an amount slightly less than an equimolar amount to the diglycolic anhydride is dissolved in dichloromethane. The solution is mixed with the suspension at 0 to 30° C. As diglycolic anhydride reacts, the mixed solution becomes clear. The reaction is completed when the solution becomes clear. This is followed by removal of water-soluble impurities by washing with deionized water, removal of water with a dehydrating agent (e.g., sodium sulfate), filtration, and solvent removal. Recrystallization from hexane is repeated plural times for purification, yielding the desired product (Patent Document 1: JP-A 2007-327085).

This synthesis method uses as the reaction solvent dichloromethane which is one of the harmful substances listed in the Chemical Substance Examination Law, Labor Safety and Health Regulations, Air Pollution Control Act, Water Pollution Control Act, Pollutant Release and Transfer Register (PRTR) and the like in Japan. It is recommended to avoid the substance. In addition, since the solubility of the reactant, diglycolic anhydride is not so high, the synthesis reaction becomes a solid-liquid reaction and has a poor reactivity.

In fact, the above known synthesis method gives a yield of more than 90% because it is conducted only on a laboratory scale where the amount of synthesis is several grams. However, a prominent drop of yield occurs when the synthesis is enlarged to a scale of several kilograms or more. In fact, in a synthesis experiment conducted on a scale of several hundreds of grams, the yield decreases below 80%. Such a yield drop is unwanted.

Further, since diglycolic anhydride is a relatively expensive chemical, the price of dialkyl diglycol amic acid synthesized therefrom is at least 3 times the price of commercially available metal extractants. This method has a significant effect of enhancing process efficiency due to excellent separation capability, but does not lead to a cost reduction of the overall process because of the increased expense of metal extractant.

CITATION LIST

Patent Document

Patent Document 1: JP-A 2007-327085

SUMMARY OF INVENTION

Technical Problem

While the invention is made to overcome the outstanding problems, its object is to provide a method for synthesizing a rare earth metal extractant without a need for diglycolic anhydride as the reactant and dichloromethane as the reaction solvent in the prior art method while achieving advantages including improved yield of synthesized product, improved efficiency of synthesis process, and reduced cost of the desired metal extractant, dialkyl diglycol amic acid.

Solution to Problem

The inventors made extensive investigations to solve the outstanding problems. With respect to the synthesis of a dialkyl diglycol amic acid serving as a rare earth metal extractant, the inventors have found that in the step of reacting a reaction intermediate product, which is obtained by reacting a reactant, diglycolic acid in an esterifying agent and then removing in vacuum the unreacted esterifying agent and the reaction residue, with a dialkylamine, if the ester formed is not isolated from the reaction intermediate product and a nonpolar or low-polar solvent which will serve as an organic solvent to form an organic phase in subsequent solvent extraction and which is capable of dissolving the dialkyl diglycol amic acid is used as the reaction solvent, then a rare earth metal extractant comprising a dialkyl diglycol amic acid as the active component can be synthesized. This method is successful in synthesizing a metal extractant in the form of dialkyl diglycol amic acid in high yields, at high efficiency and at low cost. The invention is predicated on this finding.

Accordingly, the invention provides a method for synthesizing a rare earth metal extractant as defined below.

Claim 1:

A method for synthesizing a rare earth metal extractant comprising a dialkyl diglycol amic acid having the general formula (1):

[Chemical Formula 2]

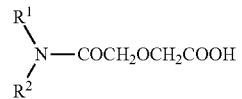

wherein $R^1$ and $R^2$ are each independently an alkyl group, at least one of $R^1$ and $R^2$ is a straight or branched alkyl group having at least 6 carbon atoms, as the active component, said method comprising the steps of:

reacting X mole of diglycolic acid with Y mole of an esterifying agent, with a molar ratio of Y/X being at least 2.5, at a reaction temperature of at least 70° C. for a reaction time of at least 1 hour, then concentrating in vacuum to remove unreacted reactant and reaction residue, thus obtaining a reaction intermediate product, adding a reaction solvent to the reaction intermediate product, the reaction solvent being a nonpolar or low-polar solvent which will serve as an organic solvent to form an organic phase during solvent extraction of rare earth metals and which is capable of dissolving the dialkyl diglycol amic acid, and reacting the reaction intermediate product with Z mole of a dialkylamine, with a molar ratio of Z/X being at least 0.9.

Claim 2:

A method for synthesizing a rare earth metal extractant according to claim 1 wherein the esterifying agent is selected from acetic anhydride and trifluoroacetic anhydride.

Claim 3:

A method for synthesizing a rare earth metal extractant according to claim 1 or 2 wherein the organic solvent to form an organic phase during solvent extraction of rare earth metals is selected from the group consisting of toluene, xylene, hexane, isododecane, kerosene, and higher alcohols.

Claim 4:

A method for synthesizing a rare earth metal extractant according to any one of claims 1 to 3 wherein in the step of reacting diglycolic acid with an esterifying agent, the molar ratio of Y/X is in the range: 2.5≤Y/X≤6.5.

Claim 5:

A method for synthesizing a rare earth metal extractant according to any one of claims 1 to 4 wherein in the step of reacting the reaction intermediate product with a dialkylamine, the molar ratio of Z/X is in the range: 0.9≤Z/X≤1.2.

Claim 6:

A method for synthesizing a rare earth metal extractant according to any one of claims 1 to 5 wherein the reaction solvent is added in such an amount that the dialkyl diglycol amic acid formed after the reactions may be present in a concentration $C_0$ of $0.1 \text{ mol/L} \leq C_0 \leq 1.5 \text{ mol/L}$.

Advantageous Effects of Invention

According to the rare earth metal extractant synthesis method of the invention, a dialkyl diglycol amic acid, which is effective for the separation of light rare earth elements, can be synthesized at high efficiency and low cost and in high yields without a need for expensive diglycolic anhydride and harmful dichloromethane. The method is of great worth in the industry.

DESCRIPTION OF EMBODIMENTS

Figure 1:
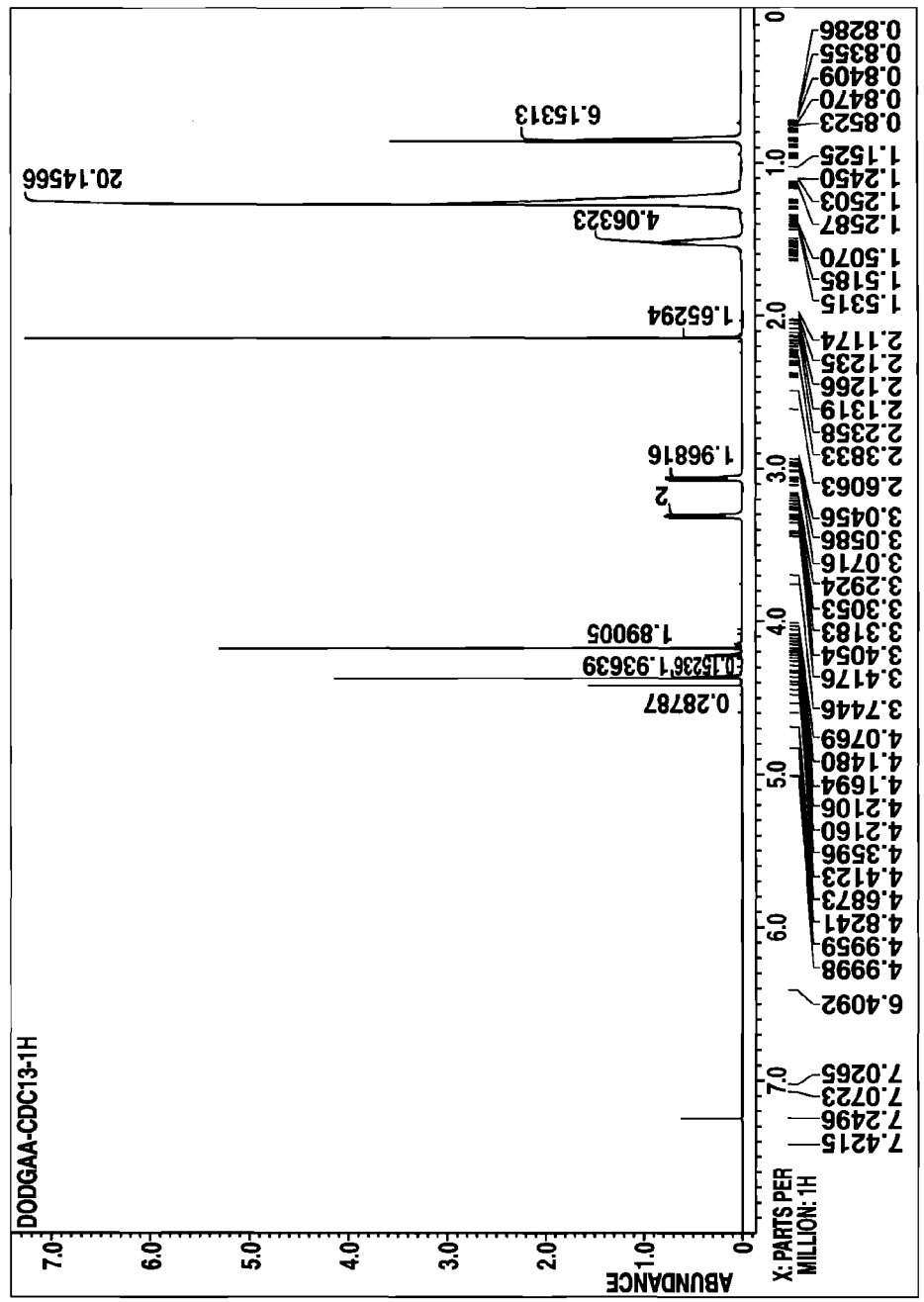
FIG. 1 is a $^1$H-NMR (in solvent CDCl$_3$) chart of the reaction product DODGAA synthesized in Example 1.

Now the invention is described in detail.
The invention pertains to a rare earth metal extractant which comprises a dialkyl diglycol amic acid having the general formula (1) as the active component.

[Chemical Formula 3]

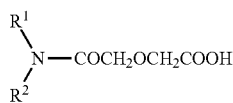

(1)

Herein $R^1$ and $R^2$ are each independently alkyl, and at least one of $R^1$ and $R^2$ is a straight or branched alkyl group of at least 6 carbon atoms, preferably 6 to 18 carbon atoms, and more preferably 7 to 12 carbon atoms. If the carbon count is less than 6, the compound fails to play the role of extractant because it is less lipophilic so that the organic phase lacks stability and exhibits poor separation from the aqueous phase, and because the dissolution of the extractant itself in aqueous phase becomes noticeable. An excessive carbon count contributes to no improvements in basic abilities like extraction and separation abilities despite the increased cost of extractant manufacture. As long as lipophilic nature is ensured, if one of $R^1$ and $R^2$ has a carbon count of at least 6, then the other may be of less than 6 carbon atoms. Preferred examples include a compound of formula (1) wherein two octyl (—C$_8$H$_{17}$) groups are introduced, which is named N,N-dioctyl-3-oxapentane-1,5-amic acid or dioctyl diglycol amic acid (abbreviated as DODGAA, hereinafter); and a compound of formula (1) wherein two 2-ethylhexyl (—CH$_2$CH(C$_2$H$_5$)C$_4$H$_9$) groups are introduced, which is named N,N-bis(2-ethylhexyl)-3-oxapentane-1,5-amic acid or di(2-ethylhexyl) diglycol amic acid (abbreviated as D2EHDGAA, hereinafter).

According to the invention, the rare earth metal extractant which comprises a dialkyl diglycol amic acid is synthesized by reacting diglycolic acid as one reactant with an esterifying agent, then concentrating in vacuum to remove a low-boiling fraction including unreacted esterifying agent and reaction residue (the esterifying agent hydrolyzate resulting from reaction of the esterifying agent with diglycolic acid), thus obtaining a reaction intermediate product, and reacting the reaction intermediate product with a dialkylamine in a reaction solvent that is a nonpolar or low-polar solvent which will serve as an organic solvent to form an organic phase during solvent extraction of rare earth metals and which is capable of dissolving the dialkyl diglycol amic acid. For example, diglycolic acid is first dissolved in the esterifying agent and aged therein. The reaction intermediate product is collected by vacuum concentration. The reaction intermediate product is suspended in an organic solvent which will form an organic phase during subsequent solvent extraction. Then the dialkylamine is dissolved in an organic solvent which will form an organic phase during subsequent solvent extraction. The suspension and the solution are mixed for reaction. The dialkylamine used herein is a secondary alkylamine having alkyl groups corresponding to $R^1$ and $R^2$ in formula (1) representative of the dialkyl diglycol amic acid.

In the synthesis method of the invention, diglycolic acid is reacted in the esterifying agent at a temperature of at least 70° C. for a time of at least 1 hour.

A reaction temperature below 70° C. provides a low reaction rate, making it difficult to achieve a conversion in excess of 90% or taking an extremely long time for sufficient reaction. Therefore, the reaction temperature is at least 70° C., preferably 70 to 140° C., and more preferably 80 to 120° C.

Also, if the reaction time is less than 1 hour, the reaction may not reach a sufficient conversion, failing to form a reaction product having a purity and yield of at least 90% both. Therefore, the reaction time is at least 1 hour, preferably 1 to 6 hours, and more preferably 2 to 4 hours.

This reaction does not quickly proceed if a molar ratio Y/X is less than 2.5 wherein the amount of diglycolic acid is X mole and the amount of the esterifying agent is Y mole. Then the reaction intermediate product and eventually the desired extractant, dialkyl diglycol amic acid are insufficient in yield and purity. The range of Y/X that ensures an acceptable yield and a purity of at least 90% is a molar ratio Y/X of at least 2.5, preferably $2.5 \leq Y/X \leq 6.5$, and more preferably $3.5 \leq Y/X \leq 5.5$.

While the intermediate product resulting from the above reaction is composed mostly of diglycolic anhydride, it contains minor amounts of unreacted diglycolic acid, esterifying agent and impurities contained in the reactant, diglycolic acid. Once the reaction of diglycolic acid with the esterifying agent is conducted by the synthesis method of the invention, the metal extractant comprising dialkyl diglycol amic acid synthesized can be obtained at a practically acceptable purity. To improve the purity of dialkyl diglycol amic acid as the metal extractant, water-soluble impurities may be removed by water washing. However, such purification is unnecessary on practical use because impurities have no impact on the capability to extract and separate rare earth metals.

The esterifying agent used herein is selected from low-boiling compounds because the reaction with the esterifying agent is followed by vacuum concentration (vacuum drying) to remove (or distil off) the unreacted reactant and reaction residue while diglycolic anhydride is left. The esterifying agent is an agent capable of dehydration and condensation of two carboxyl groups on diglycolic acid and includes, for example, acetic anhydride and trifluoroacetic anhydride. Since the synthesis method of the invention uses the esterifying agent which can be distilled off in vacuum, the method eliminates a need for the step of water washing for improving the purity of dialkyl diglycol amic acid, that is, water washing away the esterifying agent.

The reaction solvent used herein is an organic solvent to form an organic phase during subsequent solvent extraction and a nonpolar or low-polar solvent (e.g., dielectric constant≤15) which is capable of dissolving the dialkyl diglycol amic acid. A solvent having a low solubility in water, an appropriate solubility of extractant therein, a low specific gravity, and a propensity to improve the extraction capability is selected. Examples include toluene, xylene, hexane, isododecane, kerosene, and higher alcohols (e.g., straight alcohols of 5 to 8 carbon atoms). When any of these organic solvents is used as the reaction solvent, the removal of the reaction solvent is unnecessary, and it may serve as the organic phase for solvent extraction as such or if necessary, simply after an extra solvent is added so that the organic phase for solvent extraction may have the predetermined concentration of metal extractant. In contrast, if the reaction solvent is other than a nonpolar or low-polar solvent which will serve as an organic solvent to form an organic phase during subsequent solvent extraction and which is capable of dissolving the dialkyl diglycol amic acid, then the reaction solvent must be removed after the reactants are mixed and reacted.

In the metal extractant synthesis method of the invention, the ratio (Z/X) of the amount (Z mole) of dialkylamine to the amount (X mole) of diglycolic acid is at least 0.9, preferably 0.9≤Z/X≤1.2, and more preferably 0.95≤Z/X≤1.1, when the purity of diglycolic anhydride contained as the major component in the intermediate product obtained from reaction of diglycolic acid with esterifying agent and vacuum concentration is taken into account. The reaction product obtained from the inventive method contains unreacted dialkylamine as well as the desired dialkyl diglycol amic acid. In the prior art method, purification steps such as recrystallization and decantation are performed plural times in order to remove the unreacted dialkylamine. With the inventive method, the metal extractant with residual dialkylamine may be used in solvent extraction because its separation and phase separation capabilities are not impaired at all and satisfactory extraction and separation is possible. That is, since the dialkylamine remaining in the metal extractant or the organic phase for solvent extraction does not become an inhibitory factor to extraction and separation, it is unnecessary to remove the dialkylamine as the impurity. The synthesis process is thus simplified. In addition, since any loss of the reaction product during purification such as recrystallization and decantation is minimized, the yield is improved.

In case Z/X>1.2, the reaction product may contain an excess of unreacted dialkylamine as well as the desired dialkyl diglycol amic acid. In this case, the reaction product can be used as the extractant because its separation and phase separation capabilities during solvent extraction are not impaired, but the use of an excess of dialkylamine is meaningless. This setting is not advantageous in that the cost of reactant for synthesis is increased.

In case Z/X<0.9, although the desired dialkyl diglycol amic acid is obtained as the reaction product, an excessive amount of diglycolic anhydride resulting from diglycolic acid is reacted. As a result, a noticeable amount of unreacted diglycolic acid is left in the reaction product. When solvent extraction is carried out using the metal extractant with residual diglycolic acid, not only a satisfactory separation capability is lost, but also a crud develops at the interface between organic and aqueous phases to turn white turbid, resulting in poor phase separation and inhibiting normal extraction and separation. This indicates that the diglycolic acid remaining along with the metal extractant forms a complex with a rare earth metal ion, thus inhibiting satisfactory separation and extraction. It is believed that diglycolic acid becomes an inhibitory factor to separation and extraction. To obtain diglycolic acid-free dialkyl diglycol amic acid as the rare earth metal extractant capable of normal extraction and separation, the step of removing unreacted diglycolic acid, that is, the step of removing the reaction solvent and washing the reaction product with water to remove water-soluble diglycolic acid is necessary as in the prior art method. However, on water washing, the dialkyl diglycol amic acid having a very low solubility in water may crystallize and precipitate in the solvent (for example, DODGAA has a solubility in water of $6.2 \times 10^{-6}$ mol/L). To use the crystallized dialkyl diglycol amic acid as the rare earth metal extractant, it must be filtered and dried. Thus extra steps are necessary as compared with the embodiment wherein the ratio Z/X is 0.9≤Z/X≤1.2, and the process is less efficient.

In the synthesis method of the invention, the reaction is preferably carried out in the reaction solvent which is used in such an amount that the concentration $C_0$ of dialkyl diglycol amic acid is 0.1 mol/L≤$C_0$≤1.5 mol/L at the end of reaction. Specifically, for example, the amount of dialkyl diglycol amic acid formed by synthesis reaction is previously computed from the amounts of reactants by the stoichiometry according to the reaction scheme, and the amount of the reaction solvent is adjusted such that the concentration $C_0$ of dialkyl diglycol amic acid may fall in the range: 0.1 mol/L≤$C_0$—1.5 mol/L, preferably 0.2 mol/L≤$C_0$≤1.0 mol/L. This eliminates a need to adjust the concentration during solvent extraction by adding the solvent such that the metal extractant in the organic phase may be present in the predetermined concentration applicable to the practical extraction step. Thus the reaction solvent may be directly used as the organic phase for solvent extraction.

In case extractant concentration $C_0$<0.1 mol/L, although the dialkyl diglycol amic acid is produced by synthesis, the concentration of metal extractant in the organic phase is too low during solvent extraction in an actual process, and so only those rare earth aqueous solutions having a concentration of not more than 0.03 mol/L can be treated. If so, the separation plant must be scaled up, with an increased cost. To boost the extractant concentration from the low level to a high level compliant to the practical operation is very difficult, inefficient, and unrealistic.

A setting of extractant concentration $C_0$>1.5 mol/L may be difficult, depending on the type of dialkyl diglycol amic acid contained in the metal extractant, when its solubility in the organic solvent used in the general solvent extraction process is taken into account. Then, a portion of the dialkyl diglycol amic acid which has not been dissolved in the solvent at the end of synthesis reaction can crystallize and precipitate. Although it becomes possible to dissolve the dialkyl diglycol amic acid by adding a solvent, surfactant or entrainer, this addition is not effective because the conditions for controlling the organic phase of solvent extraction for stable operation become more complex. Also, even if the metal extractant has a sufficient solubility in the organic solvent used in the solvent extraction method, it is excessive relative to the metal concentration of the aqueous phase to be extracted, and thus meaningless and uneconomical.

EXAMPLES

Examples and Comparative Examples are given below by way of illustration and not by way of limitation.

Example 1 and Comparative Example 1

A mixed solution of 54 g (0.40 mole) of diglycolic acid and 240 g (2.35 moles) of acetic anhydride was heated under reflux for 2 hours. Thereafter, the excess acetic anhydride and acetic acid formed by reaction were distilled off in vacuum. To the concentrate (reaction intermediate), 300 g of toluene was added, and then 96 g (0.40 mole) of dioctylamine was added dropwise. Stirring was continued for 2 hours at room temperature, yielding a toluene solution of the reaction product (Example 1).

A portion of the reaction product solution was taken out, concentrated in vacuum to remove the solvent, and analyzed by $^1$H-NMR spectroscopy. The reaction product was identified to be the desired DODGAA (FIG. 1). The yield of DODGAA was 96%.

In another run, 300 g of toluene was added to 54 g (0.40 mole) of diglycolic acid, and then 96 g (0.40 mole) of dioctylamine was added dropwise. Stirring was continued for 2 hours at room temperature, yielding a toluene solution of the reaction product (Comparative Example 1).

Next, an extraction/separation performance test was carried out. The concentration of DODGAA in the reaction product solution of Example 1 or Comparative Example 1 was stoichiometrically computed from the amounts of reactants and reaction solvent. The reaction product solution was diluted with toluene to form an organic solution having a DODGAA concentration of 0.3 mol/L, which might become an organic phase.

A mixed rare earth metal aqueous solution was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted in the organic phase was back extracted in the hydrochloric acid aqueous solution. The concentrations of praseodymium and neodymium in the aqueous phase and the back-extracted hydrochloric acid aqueous solution were measured by an ICP atomic emission spectrometer ICP-7500 (Shimadzu Corp.). The Nd/Pr separation factor and phase separation are reported in Table 1.

TABLE 1

|  | Esterifying agent | Nd/Pr separation factor | Phase separation |
|---|---|---|---|
| Example 1 | acetic anhydride | 2.5 | definite |
| Comparative Example 1 | nil | — | indefinite |

For the reaction product obtained in Example 1, its Nd/Pr separation factor indicative of the separation ability as a metal extractant was satisfactory, and the phase separation state was definite. For the reaction product obtained in Comparative Example 1, the phase separation state was indefinite and its Nd/Pr separation factor was unmeasurable.

Example 2 and Comparative Example 2

A mixed solution of 56 g (0.42 mole) of diglycolic acid and 240 g (2.35 moles) of acetic anhydride was heated under reflux for 4 hours. Thereafter, the excess acetic anhydride and acetic acid formed by reaction were distilled off in vacuum. To the concentrate (reaction intermediate), 300 g of hexane was added, and then 101 g (0.42 mole) of di(2-ethylhexyl) amine was added dropwise. Stirring was continued for 2 hours at room temperature, yielding a hexane solution of the reaction product (Example 2).

Figure 2:
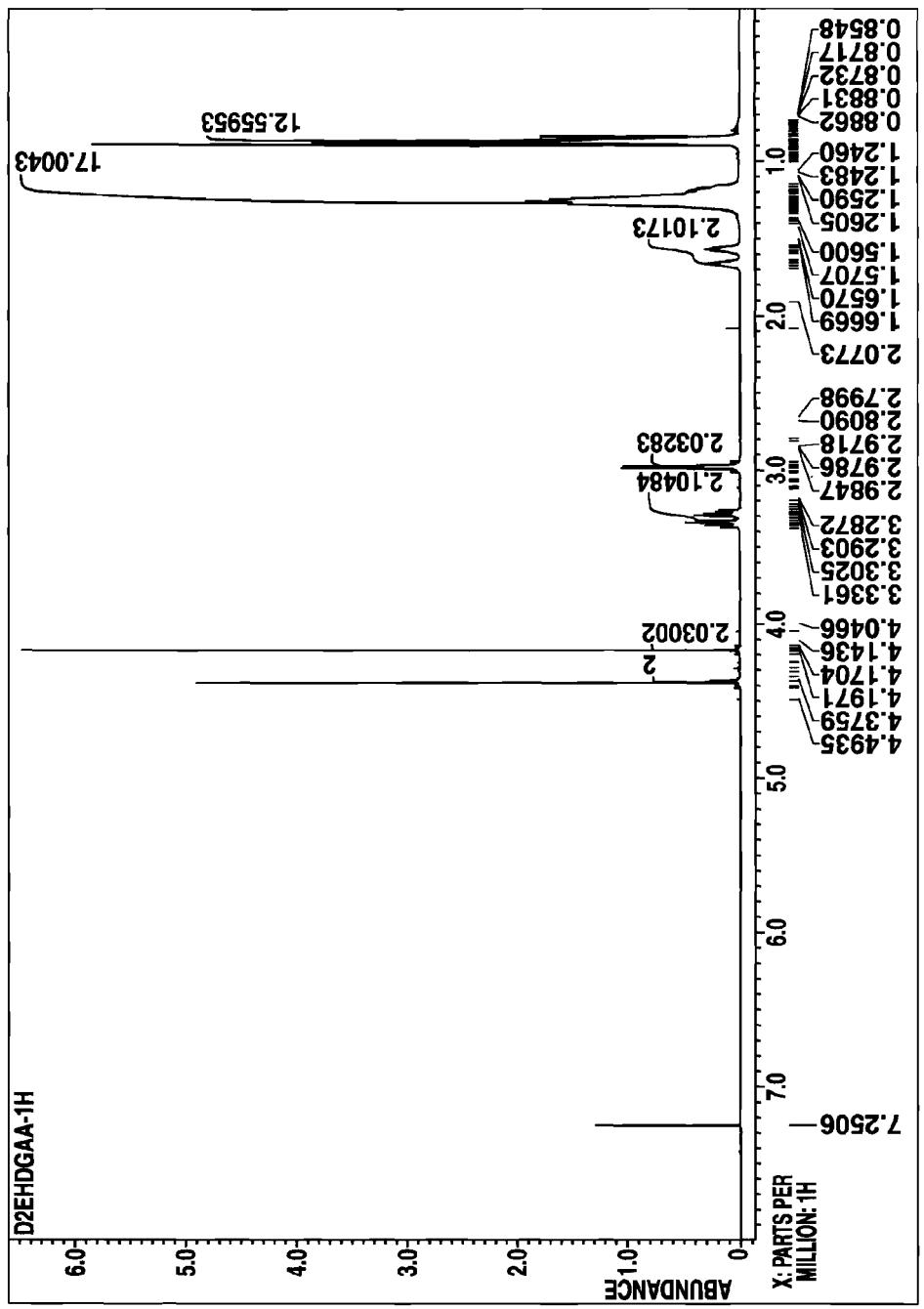
FIG. 2 is a $^1$H-NMR (in solvent CDCl$_3$) chart of the reaction product D2EHDGAA synthesized in Example 2.

A portion of the reaction product solution was taken out, concentrated in vacuum to remove the solvent, and analyzed by $^1$H-NMR spectroscopy. The reaction product was identified to be the desired D2EHDGAA (FIG. 2). The yield of D2EHDGAA was 99%.

By the same procedure as above aside from using ethanol as the reaction solvent, an ethanol solution of the reaction product was obtained (Comparative Example 2).

Next, an extraction/separation performance test was carried out. The concentration of D2EHDGAA in the reaction product solution of Example 2 or Comparative Example 2 was stoichiometrically computed from the amounts of reactants and reaction solvent. The reaction product solution was diluted with hexane to form an organic solution having a D2EHDGAA concentration of 0.3 mol/L, which might become an organic phase.

A mixed rare earth metal aqueous solution was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted in the organic phase was back extracted in the hydrochloric acid aqueous solution. The concentrations of praseodymium and neodymium in the aqueous phase and the back-extracted hydrochloric acid aqueous solution were measured by an ICP atomic emission spectrometer ICP-7500 (Shimadzu Corp.). The Nd/Pr separation factor and phase separation are reported in Table 2.

TABLE 2

|  | Reaction solvent | Nd/Pr separation factor | Phase separation |
|---|---|---|---|
| Example 2 | hexane | 2.5 | definite |
| Comparative Example 2 | ethanol | 1.4 | indefinite |

For the reaction product obtained in Example 2, its Nd/Pr separation factor indicative of the separation ability as a metal extractant was satisfactory, and the phase separation state was definite. For the reaction product obtained in Comparative Example 2, its Nd/Pr separation factor and the phase separation state were inferior to Example 2. The indefinite phase separation state indicates that the product is inadequate for solvent extraction.

Examples 3, 4 and Comparative Examples 3, 4

A mixed solution of 67 g (0.5 mole) of diglycolic acid and 255 g (2.50 moles) of acetic anhydride was heated under reflux under the conditions shown in Table 3. Thereafter, the excess acetic anhydride and acetic acid formed by reaction were distilled off in vacuum. To the concentrate (reaction intermediate), 200 g of toluene was added, and then 121 g (0.5 mole) of di(2-ethylhexyl)amine was added dropwise. Stirring was continued for 2 hours at room temperature, yielding a toluene solution of the reaction product.

Next, an extraction/separation performance test was carried out. The concentration of D2EHDGAA in the reaction product solution of Example 3, 4 or Comparative Example 3, 4 was stoichiometrically computed from the amounts of reactants and reaction solvent. The reaction product solution was diluted with toluene to form an organic solution having a D2EHDGAA concentration of 0.3 mol/L, which might become an organic phase.

A mixed rare earth metal aqueous solution was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted in the organic phase was back extracted in the hydrochloric acid aqueous solution. The concentrations of praseodymium and neodymium in the aqueous phase and the back-extracted hydrochloric acid aqueous solution were measured by an ICP atomic emission spectrometer ICP-7500 (Shimadzu Corp.). The Nd/Pr separation factor and phase separation are reported in Table 3.

TABLE 3

| | Reaction temperature (° C.) | Reaction time (hr) | Nd/Pr separation factor | Phase separation |
|---|---|---|---|---|
| Example 3 | 70 | 2 | 2.5 | definite |
| Example 4 | 120 | 4 | 2.5 | definite |
| Comparative Example 3 | 30 | 4 | 1.6 | indefinite |
| Comparative Example 4 | 120 | 0.5 | 1.8 | indefinite |

In Examples 3 and 4 wherein the conditions of reaction between diglycolic acid and acetic anhydride include a temperature of at least 70° C. and a time of at least 1 hour, their Nd/Pr separation factor indicative of the separation ability as a metal extractant and the phase separation state were satisfactory. In Comparative Examples 3 and 4 wherein the reaction conditions are outside the ranges, their Nd/Pr separation factor and the phase separation state were inferior.

Examples 5, 6 and Comparative Examples 5, 6

A mixed solution of an amount (X mole) of diglycolic acid, shown in Table 4, and an amount (Y mole) of acetic anhydride, shown in Table 4, was heated under reflux for 4 hours. Thereafter, the excess acetic anhydride and acetic acid formed by reaction were distilled off in vacuum. To the concentrate (reaction intermediate), 400 g of toluene was added, and then an amount (Z mole) of dioctylamine, shown in Table 4, was added dropwise. Stirring was continued for 2 hours at room temperature, yielding a toluene solution of the reaction product. Table 4 also reports the ratio Y/X which is the amount (Y mole) of acetic anhydride as the esterifying agent divided by the amount (X mole) of diglycolic acid and the ratio Z/X which is the amount (Z mole) of dioctylamine divided by the amount (X mole) of diglycolic acid.

Next, an extraction/separation performance test was carried out. The concentration of DODGAA in the reaction product solution of Example 5, 6 or Comparative Example 5, 6 was stoichiometrically computed from the amounts of reactants and reaction solvent. The reaction product solution was diluted with toluene to form an organic solution having a DODGAA concentration of 0.3 mol/L, which might become an organic phase.

A mixed rare earth metal aqueous solution was prepared by dissolving praseodymium chloride and neodymium chloride in water in a molar ratio Pr:Nd of 1:1 and a concentration of 0.1 mol/L of Pr+Nd to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted in the organic phase was back extracted in the hydrochloric acid aqueous solution. The concentrations of praseodymium and neodymium in the aqueous phase and the back-extracted hydrochloric acid aqueous solution were measured by an ICP atomic emission spectrometer ICP-7500 (Shimadzu Corp.). The Nd/Pr separation factor and phase separation are reported in Table 4.

TABLE 4

| | X diglycolic acid | | Y acetic anhydride | | Z dioctylamine | | Y/X | Z/X | Nd/Pr separation factor | Phase separation |
|---|---|---|---|---|---|---|---|---|---|---|
| | g | mol | g | mol | g | mol | | | | |
| Example 5 | 40.0 | 0.30 | 76.5 | 0.75 | 65.2 | 0.27 | 2.5 | 0.9 | 2.5 | definite |
| Example 6 | 40.0 | 0.30 | 199 | 1.95 | 86.9 | 0.36 | 6.5 | 1.2 | 2.5 | definite |
| Comparative Example 5 | 40.0 | 0.30 | 45.9 | 0.45 | 86.9 | 0.36 | 1.5 | 1.2 | 1.8 | indefinite |
| Comparative Example 6 | 40.0 | 0.30 | 76.5 | 0.75 | 58.0 | 0.24 | 2.5 | 0.8 | 2.0 | indefinite |

In Examples 5 and 6 wherein the amounts of diglycolic acid (X mole), acetic anhydride (Y mole) and dioctylamine (Z mole) are such that molar ratio Y/X is at least 2.5 and Z/X is at least 0.9, their Nd/Pr separation factor indicative of the separation ability as a metal extractant and the phase separation state were satisfactory. In Comparative Example 5 wherein Y/X<2.5 and Comparative Example 6 wherein Z/X<0.9, the phase separation state was indefinite because the excess diglycolic acid became an inhibitory factor to extraction, and their Nd/Pr separation factor was lower than in Examples.

Examples 7 to 9

A mixed solution of 60 g (0.45 mole) of diglycolic acid and 230 g (2.25 moles) of acetic anhydride was heated under reflux for 4 hours. Thereafter, the excess acetic anhydride and acetic acid formed by reaction were distilled off in vacuum. To the concentrate (reaction intermediate), A mL of kerosene was added, and then 109 g (0.45 mole) of di(2-ethylhexyl) amine was added dropwise. Stirring was continued for 2 hours at room temperature, yielding a kerosene solution of the reaction product. The amount (A mL) of kerosene as the reaction solvent is shown in Table 5.

A portion of the reaction product solution was taken out, concentrated in vacuum to remove the solvent, and analyzed by $^1$H-NMR spectroscopy. The reaction product was identified to be the desired D2EHDGAA. The concentration $C_O$ of the reaction product, D2EHDGAA in kerosene solution (stoichiometrically computed) is shown in Table 5.

The kerosene solution of the reaction product (D2EHDGAA) thus obtained was directly used as the organic solution serving as an organic phase, and an extraction/separation performance test was carried out as follows.

A mixed rare earth metal aqueous solution was prepared by dissolving praseodymium chloride and neodymium chloride in water in a molar ratio Pr:Nd of 1:1 and a concentration of Pr+Nd, shown in Table 5, to form an aqueous solution, which might become an aqueous phase. A separatory funnel was charged with 100 mL of the organic solution and 100 mL of the aqueous solution and shaken at 20° C. for about 20 minutes to effect extraction. After equilibrium was reached, the liquid was allowed to separate into organic and aqueous phases. A separatory funnel was charged with 100 mL of the thus separated organic phase and 100 mL of 5N hydrochloric acid and shaken at 20° C. for about 20 minutes whereby the rare earth element once extracted in the organic phase was back extracted in the hydrochloric acid aqueous solution. The concentrations of praseodymium and neodymium in the aqueous phase and the back-extracted hydrochloric acid aqueous solution were measured by an ICP atomic emission spectrometer ICP-7500 (Shimadzu Corp.). The Nd/Pr separation factor and phase separation are reported in Table 5.

TABLE 5

| | Amount A of kerosene (mL) | Concentration $C_O$ of D2EHDGAA (mol/L) | Mixed rare earth metal concentration (mol/L) | Nd/Pr separation factor | Phase separation |
|---|---|---|---|---|---|
| Example 7 | 4500 | 0.1 | 0.03 | 2.5 | definite |
| Example 8 | 560 | 0.8 | 0.25 | 2.5 | definite |
| Example 9 | 300 | 1.5 | 0.5 | 2.5 | definite |

Examples 7 to 9 wherein the D2EHDGAA concentration $C_O$ is in the range: 0.1 mol/L≤$C_O$≤1.5 mol/L showed a high separation factor and definite phase separation.

The invention claimed is:

1. A method for synthesizing a rare earth metal extractant comprising a dialkyl diglycol amic acid having the general formula (1):

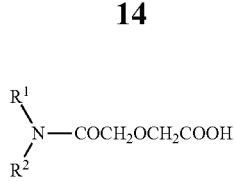

(1)

wherein $R^1$ and $R^2$ are each independently an alkyl group, at least one of $R^1$ and $R^2$ is a straight or branched alkyl group having at least 6 carbon atoms, wherein the rare earth metal extractant is contained in an organic phase for solvent extraction of rare earth metals, and wherein the organic phase comprises an organic solvent which is capable of dissolving the dialkyl diglycol amic acid, the method comprising the steps of:

reacting X mole of diglycolic acid with Y mole of an esterifying agent, with a molar ratio of Y/X being at least 2.5, at a reaction temperature of at least 70° C. for a reaction time of at least 1 hour, then concentrating in vacuum to remove unreacted reactant and reaction residue, thus obtaining a reaction intermediate product, adding the organic solvent to the reaction intermediate product, wherein the organic solvent is a nonpolar or low-polar solvent and wherein the organic solvent is to be contained in the organic phase, reacting the reaction intermediate product with Z mole of a dialkylamine, with a molar ratio of Z/X being at least 0.9, so as to obtain the rare earth metal extractant which is contained in the organic solvent, and directly extracting a rare earth metal with the organic phase, which comprises the rare earth metal extractant contained in the organic solvent, without purifying the rare earth metal extractant.

2. A method for synthesizing a rare earth metal extractant according to claim 1 wherein the esterifying agent is selected from acetic anhydride and trifluoroacetic anhydride.

3. A method for synthesizing a rare earth metal extractant according to claim 1, wherein the organic solvent is selected from the group consisting of toluene, xylene, hexane, isododecane, kerosene, and higher alcohols.

4. A method for synthesizing a rare earth metal extractant according to claim 1 wherein in the step of reacting diglycolic acid with an esterifying agent, the molar ratio of Y/X is in the range: 2.5≤Y/X≤6.5.

5. A method for synthesizing a rare earth metal extractant according claim 1 wherein in the step of reacting the reaction intermediate product with a dialkylamine, the molar ratio of Z/X is in the range: 0.9≤Z/X≤1.2.

6. A method for synthesizing a rare earth metal extractant according to claim 1 wherein the organic solvent is added in such an amount that the dialkyl diglycol amic acid formed after the reactions is present in the organic phase in a concentration $C_O$ of 0.1 mol/L≤$C_O$≤1.5 mol/L.

7. A method for synthesizing an organic phase for solvent extraction of rare earth metals, the organic phase comprising a rare earth metal extractant comprising a dialkyl diglycol amic acid having the general formula (1):

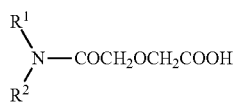

(1)

wherein $R^1$ and $R^2$ are each independently an alkyl group, at least one of $R^1$ and $R^2$ is a straight or branched alkyl group having at least 6 carbon atoms; and the organic phase further comprising an organic solvent which is capable of dissolving the dialkyl diglycol amic acid, the method comprising the steps of:

reacting X mole of diglycolic acid with Y mole of an esterifying agent, with a molar ratio of Y/X being at least 2.5, at a reaction temperature of at least 70° C. for a reaction time of at least 1 hour, then concentrating in vacuum to remove unreacted reactant and reaction residue, thus obtaining a reaction intermediate product, adding the organic solvent to the reaction intermediate product, wherein the organic solvent is a nonpolar or low-polar solvent and wherein the organic solvent is to be contained in the organic phase, reacting the reaction intermediate product with Z mole of a dialkylamine, with a molar ratio of Z/X being at least 0.9, so as to obtain the rare earth metal extractant which is contained in the organic solvent, and directly extracting a rare earth metal with the organic phase, which comprises the rare earth metal extractant contained in the organic solvent, without purifying the rare earth metal extractant.

8. A method for synthesizing an organic phase for solvent extraction of rare earth metals according to claim 7, wherein the esterifying agent is selected from acetic anhydride and trifluoroacetic anhydride.

9. A method for synthesizing an organic phase for solvent extraction of rare earth metals according to claim 7, wherein the organic solvent is selected from the group consisting of toluene, xylene, hexane, isododecane, kerosene, and higher alcohols.

10. A method for synthesizing an organic phase for solvent extraction of rare earth metals according to claim 7, wherein in the step of reacting diglycolic acid with the esterifying agent, the molar ratio of Y/X is in the range: $2.5 \leq Y/X \leq 6.5$.

11. A method for synthesizing an organic phase for solvent extraction of rare earth metals according to claim 7, wherein in the step of reacting the reaction intermediate product with the dialkylamine, the molar ratio of Z/X is in the range: $0.9 \leq Z/X \leq 1.2$.

12. A method for synthesizing an organic phase for solvent extraction of rare earth metals according to claim 7, wherein the organic solvent is added in such an amount that the dialkyl diglycol amic acid formed after the reactions is present in the organic phase in a concentration $C_0$ of $0.1 \text{ mol/L} \leq C_0 \leq 1.5 \text{ mol/L}$.

13. A method for synthesizing a rare earth metal extractant according to claim 1, wherein the organic solvent is selected from the group consisting of xylene, hexane, isododecane, kerosene, and higher alcohols.

14. A method for synthesizing a rare earth metal extractant according to claim 1, wherein the straight or branched alkyl group has 6 to 12 carbon atoms.

15. A method for synthesizing a rare earth metal extractant according to claim 1, wherein the reaction intermediate product obtained by concentrating in vacuum is directly used in the adding step.

16. A method for synthesizing a rare earth metal extractant according to claim 1, wherein the reaction intermediate product obtained by concentrating in vacuum is provided to the adding step without purification.

17. A method for synthesizing an organic phase for solvent extraction of rare earth metals according to claim 7, wherein the organic solvent is selected from the group consisting of xylene, hexane, isododecane, kerosene, and higher alcohols.

18. A method for synthesizing an organic phase for solvent extraction of rare earth metals according to claim 7, wherein the straight or branched alkyl group has 6 to 12 carbon atoms.

19. A method for synthesizing an organic phase for solvent extraction of rare earth metals according to claim 7, wherein the reaction intermediate product obtained by concentrating in vacuum is directly used in the adding step.

20. A method for synthesizing an organic phase for solvent extraction of rare earth metals according to claim 7, wherein the reaction intermediate product obtained by concentrating in vacuum is provided to the adding step without purification.

21. A method for extraction of a rare earth metal with an organic phase, which comprises a rare earth metal extractant and an organic solvent, for solvent extraction of the rare earth metal, wherein the rare earth metal extractant comprises a dialkyl diglycol amic acid having the general formula (1):

wherein $R^1$ and $R^2$ are each independently an alkyl group, at least one of $R^1$ and $R^2$ is a straight or branched alkyl group having at least 6 carbon atoms, wherein the organic solvent is capable of dissolving the dialkyl diglycol amic acid, the method comprising the steps of:

reacting X mole of diglycolic acid with Y mole of an esterifying agent, with a molar ratio of Y/X being at least 2.5, at a reaction temperature of at least 70° C. for a reaction time of at least 1 hour, then concentrating in vacuum to remove unreacted reactant and reaction residue, thus obtaining a reaction intermediate product, adding the organic solvent to the reaction intermediate product, wherein the organic solvent is a nonpolar or low-polar solvent and wherein the organic solvent is to be contained in the organic phase, reacting the reaction intermediate product with Z mole of a dialkylamine, with a molar ratio of Z/X being at least 0.9, so as to obtain the rare earth metal extractant which is contained in the organic solvent, and directly extracting the rare earth metal with the organic phase without purifying the rare earth metal extractant.

22. A method according to claim 21, wherein the esterifying agent is selected from acetic anhydride and trifluoroacetic anhydride.

23. A method according to claim 21, wherein the organic solvent is selected from the group consisting of toluene, xylene, hexane, isododecane, kerosene, and higher alcohols.

24. A method according to claim 21, wherein in the step of reacting diglycolic acid with an esterifying agent, the molar ratio of Y/X is in the range: $2.5 \leq Y/X \leq 6.5$.

25. A method according to claim 21, wherein in the step of reacting the reaction intermediate product with a dialkylamine, the molar ratio of Z/X is in the range: $0.9 \leq Z/X \leq 1.2$.

26. A method according to claim 21, wherein the organic solvent is added in such an amount that the dialkyl diglycol amic acid formed after the reactions is present in the organic phase in a concentration $C_0$ of $0.1 \text{ mol/L} \leq C_0 \leq 1.5 \text{ mol/L}$.

27. A method according to claim 21, wherein the organic solvent is selected from the group consisting of xylene, hexane, isododecane, kerosene, and higher alcohols.

28. A method according to claim 21, wherein the straight or branched alkyl group has 6 to 12 carbon atoms.

29. A method of claim 21, wherein the reaction intermediate product obtained by concentrating in vacuum is directly used in the adding step.

30. A method of claim 21, wherein the reaction intermediate product obtained by concentrating in vacuum is provided to the adding step without purification.

* * * * *